(12) United States Patent
Rodelet

(10) Patent No.: US 6,432,912 B1
(45) Date of Patent: Aug. 13, 2002

(54) HOMOGENEOUS LIQUID FRAGRANCING COMPOSITION BASED ON VOLATILE SILICONES

(75) Inventor: Jean-François Rodelet, Boulogne (FR)

(73) Assignee: Caster, Paris (FR)

( * ) Notice: Subject to any disclaimer, the term of this patent is extended or adjusted under 35 U.S.C. 154(b) by 0 days.

(21) Appl. No.: 09/544,939

(22) Filed: Apr. 7, 2000

(30) Foreign Application Priority Data

Apr. 7, 1999 (FR) .............................. 99 04315

(51) Int. Cl.[7] .................................................. A61K 7/46
(52) U.S. Cl. ........................................ 512/1; 424/76.4
(58) Field of Search ............................. 512/1; 424/76.4

(56) References Cited

U.S. PATENT DOCUMENTS

| | | | |
|---|---|---|---|
| 5,013,763 A | 5/1991 | Tubesing et al. | 514/772 |
| 5,468,725 A * | 11/1995 | Guenin et al. | 512/2 |
| 5,738,841 A | 4/1998 | Mellul et al. | 424/59 |
| 6,248,339 B1 * | 6/2001 | Knitowski et al. | 424/401 |

FOREIGN PATENT DOCUMENTS

| | | |
|---|---|---|
| EP | 0723 776 A1 | 7/1996 |
| WO | 9603962 A1 | 2/1996 |

* cited by examiner

*Primary Examiner*—Jill Warden
*Assistant Examiner*—Monique T. Cole
(74) *Attorney, Agent, or Firm*—O'Keefe, Egan & Peterman, LLP

(57) ABSTRACT

The present invention relates to an alcohol-free, homogeneous liquid fragrancing composition consisting of a fragrancing base dissolved in a volatile liquid support comprising at least one volatile silicone and at least one first co-solvent chosen from esters of $C_{4-15}$ alcohols and of $C_{4-10}$ carboxylic acids and, optionally, at least one second co-solvent chosen from certain diesters of oligomeric polyethylene glycol.

15 Claims, No Drawings

HOMOGENEOUS LIQUID FRAGRANCING COMPOSITION BASED ON VOLATILE SILICONES

The present invention relates to an alcohol-free, homogeneous liquid fragrancing composition in which the odoriferous molecules are dissolved in one or more volatile silicones by means of the presence of suitable co-solvents.

Perfumery products such as perfumes, eaux de toilette, eaux de parfum, etc., conventionally consist of a fragrancing base, which is a complex mixture of odoriferous molecules of natural or synthetic origin, dissolved in ethanol or in an aqueous-alcoholic mixture with a low water content.

However, these alcohol-based products can cause adverse reactions in certain users, such as poor skin tolerance or drying of the skin. They moreover present a hazard in the event of accidental ingestion by children and are subject to special monitoring, in particular in the United States, following the recent sensitization of public opinion to ecological problems resulting from the emission of volatile organic products into the atmosphere.

Consequently, attempts have been made to dissolve fragrancing bases in water using suitable surfactants such a polyethoxylated castor oil. The compositions thus obtained have been marketed in the form of eaux de toilette intended essentially for children.

Large amounts of surfactants are required and, although the fragrancing products thus obtained are clear, they are highly foaming and feel very sticky on the skin.

Another approach consists in dissolving the fragrancing base in a plant oil or a mixture of plant oils. The drawback of this formulation is that it is very greasy, leaving an unpleasant film on the skin which can stain clothing.

The aim of the present invention was to develop an alcohol-free, homogeneous liquid fragrancing composition which has satisfactory cosmetic and organoleptic properties (no greasy feel, no drying or irritation of the skin, pleasant appearance, non-foaming product, etc.) and whose volatility is comparable to that of the existing alcohol-based compositions.

This object has been achieved by means of the use of one or more linear or cyclic volatile silicones in combination with one or more suitable specific co-solvents, as volatile liquid support capable of dissolving the known fragrancing bases usually used in perfumery.

One subject of the present invention is thus an alcohol-free, homogeneous liquid fragrancing composition consisting of a fragrancing base dissolved in a volatile liquid support comprising at least one volatile silicone and at least one first co-solvent chosen from esters of $C_{4-15}$ alcohols and of $C_{4-10}$ carboxylic acids and, optionally, at least one second co-solvent chosen from certain diesters of oligomeric polyethylene glycol.

A subject of the invention is also a process for preparing such an alcohol-free, homogeneous liquid fragrancing composition, which consists in dissolving a fragrancing base in a volatile support comprising at least one volatile silicone, using, as solubilizing agent
  at least one first co-solvent of ester type as defined below and, optionally,
  at least one second co-solvent of oligomeric ethylene glycol diester type as defined below.

A subject of the invention is also the use of at least one first co-solvent of ester type as defined below, or a combination of at least one first co-solvent of ester type and at least one second co-solvent of oligomeric ethylene glycol diester type as defined below, for dissolving a fragrancing base in a liquid support based on volatile silicones.

Another subject of the invention is the use in perfumery of an alcohol-free, homogeneous liquid fragrancing composition as described above.

In the present invention, the expression "volatile silicone" means silicones having a vapour pressure, measured at 25° C., at least equal to 5 pascals, preferably at least equal to 10 pascals.

The volatile silicones which can be used as volatile liquid support for perfumery products according to the present invention are preferably chosen from linear polydimethylsiloxanes corresponding to the formula

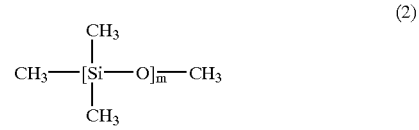

in which m is equal to 2, 3, 4 or 5, and cyclic polydimethylsiloxanes corresponding to the formula

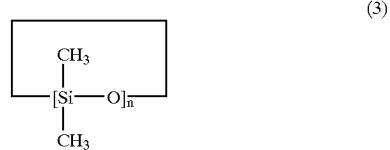

in which n is 4, 5 or 6.

Beyond the degree of polymerization n or m indicated above, i.e. above 5 —Si(CH$_3$)—O— units for the linear siloxanes and 6 —Si(CH$_3$)—O— units for the cyclic siloxanes, the silicones are generally not volatile enough to be able to be used in the present invention.

These silicones can be used alone or in the form of mixtures. They are fully miscible with each other in all proportions. It is thus possible to adjust the rate of evaporation of a liquid support for perfumes by combining, for example, a relatively non-volatile silicone which has a high degree of polymerization with a highly volatile silicone of low mass.

In the group of silicones above, linear octamethyltrisiloxane (L$_3$), linear decamethyltetra-siloxane (L$_4$), cyclic octamethyltetrasiloxane (D$_4$) and cyclic decamethylpentasiloxane (D$_5$) are preferred in particular.

These silicones or mixtures of silicones are generally too hydrophobic to be able to dissolve the fragrancing bases used in perfumery. It has thus been necessary to add suitable solubilizing agents, referred to hereinbelow as co-solvents, i.e. compounds which, when used in low proportion relative to the silicones, give a homogeneous perfume/silicone solution.

These co-solvents should not only have good power for dissolving odoriferous molecules, but should also be non-toxic and should have satisfactory cosmetic properties (absence of greasy, shiny or sticky residues).

After numerous solubilization tests, the Applicant has been able to select a group of organic solvents of ester type which, alone or in combination, satisfy the criteria stated above.

Thus, when the fragrancing base is relatively apolar, the co-solvent used is one or more esters of $C_{4-15}$ alcohols and of C4-10 carboxylic acids.

The alcohols are aliphatic primary alcohols, containing a linear or branched chain comprising from 4 to 15 carbon atoms. Mention may be made, by way of example, of butanol, pentanol, hexanol, heptanol, octanol, decyl alcohol, dodecyl alcohol, tetradecyl alcohol or pentadecyl alcohol.

The acids are aliphatic, cycloaliphatic or aromatic carboxylic acids comprising from 4 to 10 carbon atoms, among which benzoic acid is most particularly preferred.

The co-solvents of this first type which are particularly advantageous are alkyl benzoates containing a linear or branched $C_{12-15}$ chain, and dodecyl benzoate is most particularly preferred.

Moreover, when the fragrancing base has considerable polarity, it may be necessary to combine this first type of co-solvent with a second type of co-solvent chosen from the polyethylene glycol diesters of formula

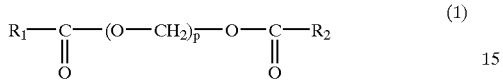

(1)

in which $R_1$ and $R_2$, which may be identical or different, each represent a $C_{6-12}$ alkyl group and p is equal to 3, 4 or 5.

One diester which is particularly preferred as a second co-solvent is tetraethylene glycol diheptanoate.

The co-solvent content in the final composition will obviously depend on the chemical nature and the amount of odoriferous molecules to be dissolved, the silicone(s) chosen as volatile support, the chemical nature of the co-solvent(s) and the weight ratio of the first co-solvent to the second co-solvent which may be present.

In general, the final fragrancing composition contains from 0.5 to 10 parts by weight of co-solvent(s) per 1 part by weight of fragrancing base.

The fraction of co-solvent generally does not exceed 25% by weight of the final composition.

The weight ratio of the first co-solvent to the second co-solvent, when the latter is present, is between 1/1 and 100/1, preferably between 2/1 and 30/1.

The fragrancing bases which can thus be dissolved in a volatile silicone/co-solvent(s) support are chosen from the fragrancing bases usually used in perfumery. These are complex mixtures produced by perfumers, composed of natural essential oils (extracts of flowers, of plants or of certain animal organs) optionally combined with odoriferous molecules obtained by synthesis.

The fragrancing composition of the present invention can be used as an eau de toilette, eau de parfum, perfume or aftershave lotion.

The present invention will be described in greater detail with the aid of the examples which follow, which are purely illustrative in nature.

| Example 1 | |
|---|---|
| Fragrancing base composed mainly of essence of gardenia, of jasmine and of rose | 10% by weight |
| Dodecyl benzoate | 10% by weight |
| Tetraethylene glycol diheptanoate | 8% by weight |
| Hexamethyldisiloxane | qs 100% by weight |
| Example 2 | |
| Fragrancing base composed mainly of essences of iris, of vanilla and of sandalwood | 8% by weight |
| Dodecyl benzoate | 3% by weight |
| Tetraethylene glycol diheptanoate | 1% by weight |
| Octamethyltetracyclosiloxane | qs 100% by weight |

-continued

| Example 3 | |
|---|---|
| Fragrancing base composed mainly of essences of mimosa, of vanilla and of musk | 12% by weight |
| Dodecyl benzoate | 8% by weight |
| Tetraethylene glycol diheptanoate | 2% by weight |
| Octamethyltrisiloxane | 45% by weight |
| Octamethyltetracyclosiloxane | qs 100% by weight |
| Example 4 | |
| Fragrancing base composed mainly of essences of neroli, of tuberose and of vetiver | 6% by weight |
| Dodecyl benzoate | 8% by weight |
| Tetraethylene glycol diheptanoate | 4% by weight |
| Decamethylpentacyclosiloxane | 10% by weight |
| Hexamethyldisiloxane | qs 100% by weight |
| Example 5 | |
| Fragrancing base composed mainly of essences of lavender, of vanilla and of bergamot | 6% by weight |
| Dodecyl benzoate | 12% by weight |
| Tetraethylene glycol diheptanoate | 4% by weight |
| Octamethyltetracyclosiloxane | 68% by weight |
| Decamethylpentacyclosiloxane | 8% by weight |
| Dodecamethylhexacyclosiloxane | 2% by weight |
| Example 6 | |
| Essential oil of lavender | 6% by weight |
| Dodecyl benzoate | 10% by weight |
| Tetraethylene glycol diheptanoate | 0.1% by weight |
| Octamethyltrisiloxane | qs 100% by weight |

I claim:

1. Alcohol-free, homogenous liquid fragrancing composition which comprises a fragrancing base dissolved in a volatile liquid support, wherein the volatile liquid support comprises at least one volatile silicone and
   at least one first co-solvent chosen from esters of $C_{4-15}$ alcohols and of $C_{4-10}$ carboxylic acids and, optionally,
   at least one second co-solvent chosen from the diesters of formula

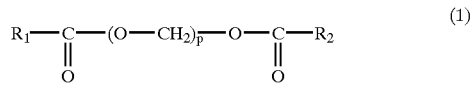

(1)

in which $R_1$, and $R_2$, which may be identical or different, represent a $C_{6-12}$ alkyl group and p is equal to 3, 4 or 5.

2. Fragrancing composition according to claim 1, characterized in that the volatile silicone(s) is(are) chosen from linear polydimethylsiloxanes corresponding to the formula

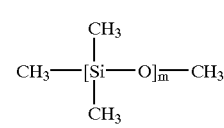

(2)

in which m is equal to 2, 3, 4 or 5, and the cyclic polydimethylsiloxanes corresponding to the formula

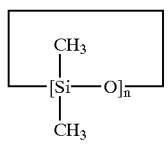
(3)

in which n is 4, 5 or 6.

3. Fragrancing composition according to claim 1 characterized in that the volatile silicone(s) is(are) chosen from linear octamethyltrisiloxane ($L_3$), linear decamethyltetrasiloxane ($L_4$), cyclic octamethyltetrasiloxane ($D_4$) and cyclic decamethylpentasiloxane ($D_5$).

4. Fragrancing composition according to claim 1 characterized in that the said first co-solvent is an alkyl benzoate containing a linear or branched $C_{12-15}$ chain.

5. Fragrancing composition according to claim 4, characterized in that the said first co-solvent is dodecyl benzoate.

6. Fragrancing composition according to claim 1 characterized in that the said second co-solvent is tetraethylene glycol diheptanoate.

7. Fragrancing composition according to claim 1 characterized in that it contains from 0.5 to 10 parts by weight of co-solvent(s) per 1 part by weight of fragrancing base.

8. Fragrancing composition according to claim 1 characterized in that the fraction of co-solvent is less than 25% by weight relative to the final composition.

9. Fragrancing composition according to claim 1, characterized in that the weight ratio of the first co-solvent to the second co-solvent, when the latter is present, is between 1/1 and 100/1.

10. Fragrancing composition according to claim 1 characterized in that it is in the form of a perfume, an eau de parfum, an eau de toilette or an aftershave lotion.

11. Process for preparing an alcohol-free, homogenous liquid fragrancing composition, comprising dissolving a fragrancing base in a volatile support comprising at least one volatile silicone, using, as a solubilizing agent at least one first co-solvent chosen from esters of $C_{4-15}$ alcohols and of $C_{4-10}$ carboxylic acids and, optionally, at least one second co-solvent chosen from the diesters of formula

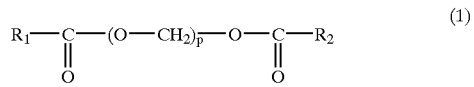
(1)

in which $R_1$ and $R_2$, which may be identical or different, represent a $C_{6-12}$ alkyl group and p is equal to 3, 4 or 5.

12. Fragrancing composition according to claim 1, characterized in that the weight ratio of the first co-solvent to the second co-solvent, when the latter is present, is between 2/1 and 30/1.

13. Method of use in perfumery of a composition as defined in claim 1.

14. A method of use in perfumery of a composition as defined in claim 1, comprising applying the composition to human skin.

15. A method which comprises combining a fragrance base, a liquid support, and a solubilizing agent which comprises at least one volatile silicone, at least one first co-solvent selected from the group consisting of esters of $C_{4-15}$ alcohols and of $C_{4-10}$ carboxylic acids, and, optionally, at least one second co-solvent of formula

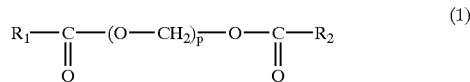
(1)

wherein $R_1$ and $R_2$, which may be identical or different, represent a $C_{6-12}$ alkyl group and p is equal to 3, 4, or 5.

* * * * *